United States Patent [19]
Phan et al.

[11] Patent Number: 5,257,832
[45] Date of Patent: Nov. 2, 1993

[54] UNIVERSAL TUBE CONNECTOR

[75] Inventors: Cu N. Phan; Marshall L. Stoller, both of San Francisco, Calif.

[73] Assignee: The Regents of the University of California, Oakland, Calif.

[21] Appl. No.: 880,217

[22] Filed: May 7, 1992

[51] Int. Cl.$^5$ .................................... F16L 25/00
[52] U.S. Cl. .............................. 285/177; 285/293; 285/915; 604/240; 604/283; 604/243
[58] Field of Search ............ 604/240, 241, 243, 283; 128/364; 285/177, 915, 293

[56] References Cited

U.S. PATENT DOCUMENTS

| | | | |
|---|---|---|---|
| 662,618 | 11/1900 | Camp | 285/293 |
| 2,924,546 | 2/1960 | Shaw | 285/293 X |
| 3,096,763 | 7/1963 | McConnaughey et al. | 604/240 |
| 3,523,532 | 8/1970 | Burke | 604/240 |
| 3,756,235 | 9/1973 | Burke et al. | 604/240 |
| 4,037,599 | 7/1977 | Raulerson | 604/283 X |
| 4,040,421 | 8/1977 | Young | 604/243 X |
| 4,114,626 | 9/1978 | Beran | 285/177 X |
| 4,266,815 | 5/1981 | Cross | 285/330 |
| 4,346,704 | 8/1982 | Kulle | 128/214 |
| 4,776,849 | 10/1988 | Shinno et al. | 604/283 |
| 4,842,591 | 6/1989 | Luther | 604/283 |
| 4,874,378 | 10/1989 | Hillstead | 604/167 |
| 4,935,010 | 6/1990 | Cox et al. | 604/122 |
| 5,071,413 | 12/1991 | Utterberg | 604/283 |

FOREIGN PATENT DOCUMENTS 2019219A 4/1979 United Kingdom.
2088530A 10/1980 United Kingdom.

Primary Examiner—Eric K. Nicholson
Assistant Examiner—Heather Chun
Attorney, Agent, or Firm—Townsend and Townsend Khourie and Crew

[57] ABSTRACT

The invention relates generally to connecting tubes for medical use. A connector (1) having a conical hollow body (2) and a pierceable sealing diaphragm (10) is attached to a flexible tail portion (12) comprised of two co-operating adhesive-coated strips (24/26). The adhesive on inner surfaces (20) of the strips is protected by peel-away coverings (14) prior to use. In use, a medical tube (16) is introduced into the body through an end (6) and through the sealing diaphragm. The adhesive strips contact the tube to further secure it to the body. Another device, such as a second tube or a drainage bag, connects to the other end (4) of the body.

15 Claims, 2 Drawing Sheets

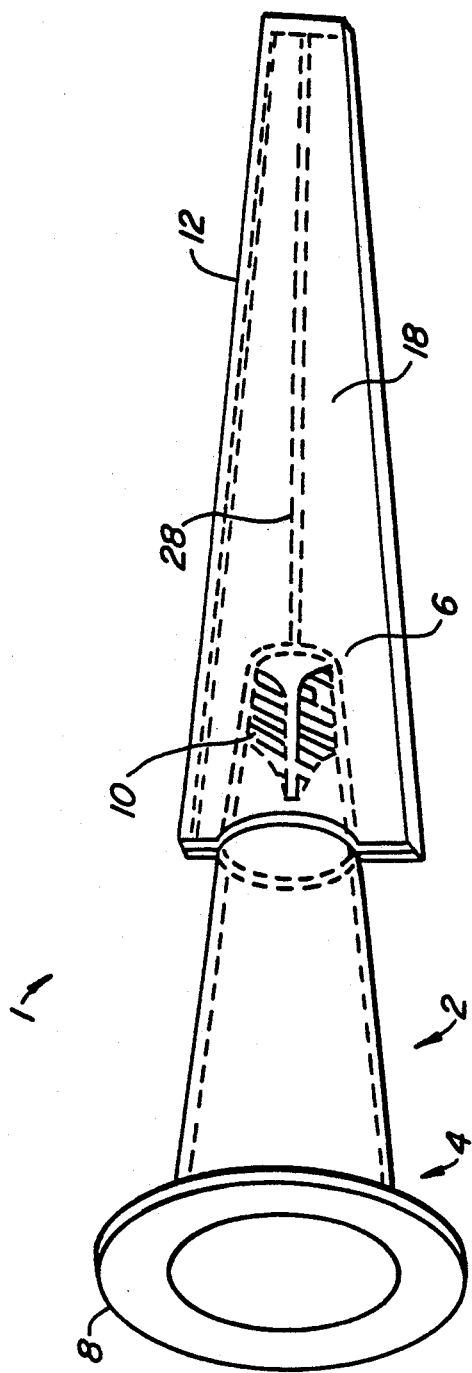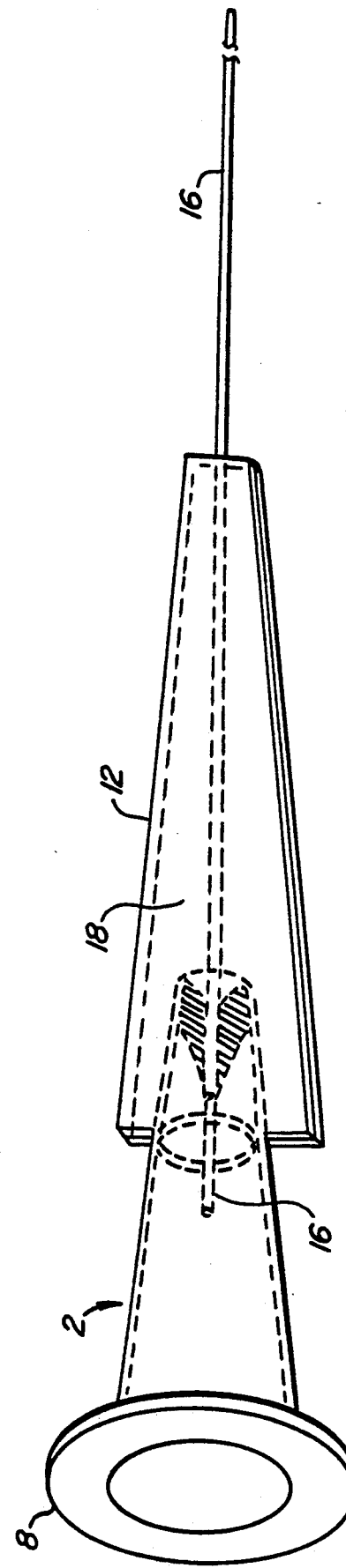

UNIVERSAL TUBE CONNECTOR

BACKGROUND OF THE INVENTION

The invention relates generally to connecting tubes for medical use. Examples are tubes exiting from a patient to an appropriate device such as a pump or collection vessel for drainage fluid. Some of the problems in the prior art include leakage, kinking, obstruction, dislodgement, poor access, difficult assembly and the unavailability of a suitably sized connector.

A common goal of various disciplines within medicine and surgery is to keep naturally open anatomical structures open. When these structures are compromised, or occluded from external compression, internal occlusion or other problems, prosthetic tubes are often placed to establish drainage. The energy and resources required to place such prosthetic tubes are frequently lost due to poor or inadequate connectors to appropriate collecting devices. These tubes are frequently of small caliber and brought to an external collecting device by means of a larger drainage tube.

The presently available connectors generally fall into two broad categories. Connectors in one category use external compression to maintain an effective seal. An example of this group is a nipple connector which generally has a plastic diaphragm with a central slit. Another example is a screw-compression variety which usually has a plastic washer compressed by means of a two-part screw mount. The other broad category of presently available connectors includes the internal male-to-female type connectors, typically having a conical shape.

Some of the problems with the presently available connectors are the following. A seal may be made inadequately in an attempt to prevent obstruction. This would result in leakage. Similarly, lack of adhesion between the connector and the tube would result in leakage.

When a small tube is connected to a larger tube, problems of kinking can occur. This may result from an acute transition between the tube diameters or between the relative stiffness of the tubes. Obstruction of the tube may be caused by decreasing luminal diameter secondary to excessive extrinsic compression from the connector. The excessive compression may have been placed in an attempt to prevent dislodgement and leakage. Also, obstruction can occur from decreasing luminal diameter secondary to an internal luminal connector.

Additional problems are dislodgement of the connector, either from the tube which goes to the patient or from a tube which goes to some other external device. Unavailability of a suitable connector to properly fit a particular tube may also cause problems with connection, particularly leakage. Access for irrigation or drainage may be poor and sometimes assembly is difficult.

SUMMARY OF THE INVENTION

A universal tube connector of the present invention has a hollow tubular body including first and second open ends. A tail portion is attached to the body in an area including the second open end. The body is usually conical in shape. A first seal is mounted to, and preferably in, the body and is adapted to seal the region between the body and a medical tube when the tube is inserted into the body and through the first seal. Alternatively, the first seal could be positioned substantially outside the hollow body abutting the second open end.

The first seal can be a diaphragm which is pierceable by the tubing. The diaphragm may be a thin membrane, but more typically it resembles a thickened plug provided with a central aperture. The aperture is smaller than the narrowest tube it is intended to accommodate. The area around the aperture is distensible and elastic so that the tube can be admitted through the aperture without a gap between the tube and the aperture. Other arrangements are possible for the first seal. For instance, a pierceable plug without an aperture could be employed.

The tail preferably provides two functions: it secures the tube to the body and acts as a second seal. The tail has an adhesive surface positioned to adhesively contact the tube when the tube engages the first seal to help secure the tubing to the connector. Usually the tail is elongated and tapered with a wider portion towards the area of the tail attached to the body and a narrower part extending past the body away from the first end. The tail may have two co-operating halves having inner surfaces adapted to contact the medical tubing. These inner surfaces are provided with the adhesive material to bind the tail to the tubing. Usually the adhesive material is protected with a peel-away cover which is removed to expose the adhesive for use.

The connector is typically formed of synthetic materials. The hollow body is generally formed of a plastic such as polyethylene or polypropylene. The diaphragm is usually formed of an elastomeric material. Alternatively it could be a displaceable packing material or some other arrangement. The flexible tail could be formed of a variety of materials, such as polyolefin or other plastics, although other materials may be suitable.

The inner surfaces of the cooperating tail portions may be provided with any of a number of adhesives known in the art. Examples are starch, gum, glue, bone, cellulose acetate, casein, sodium silicate, latex, resin, epoxy, and mastic.

Some advantages of the invention are that one size of connector accommodates different sizes of tubes and the conical body easily connects to a drainage bag such as a Foley bag. The dual seals provided by the diaphragm and adhesive tail provide double protection against leakage and dislodgement. The connector obviates the need for secondary and tertiary connecting means and also reduces kinking. Any compromise of the medical tubing's lumen is minimized or nonexistent.

The device is small, compact, inexpensive to manufacture and easy to use. A preferred application is to connect Foley catheters to drainage bags, but additional uses are evident. For example, connections to chest tubes, suction pumps, peritoneal drainage, and wound drainage can be facilitated by this invention.

BRIEF DESCRIPTION OF THE DRAWINGS

FIG. 1 depicts a universal connector constructed in accordance with the present invention;

FIG. 3 shows a device according to the present invention in use.

DESCRIPTION OF THE PREFERRED EMBODIMENT

Figure 2:
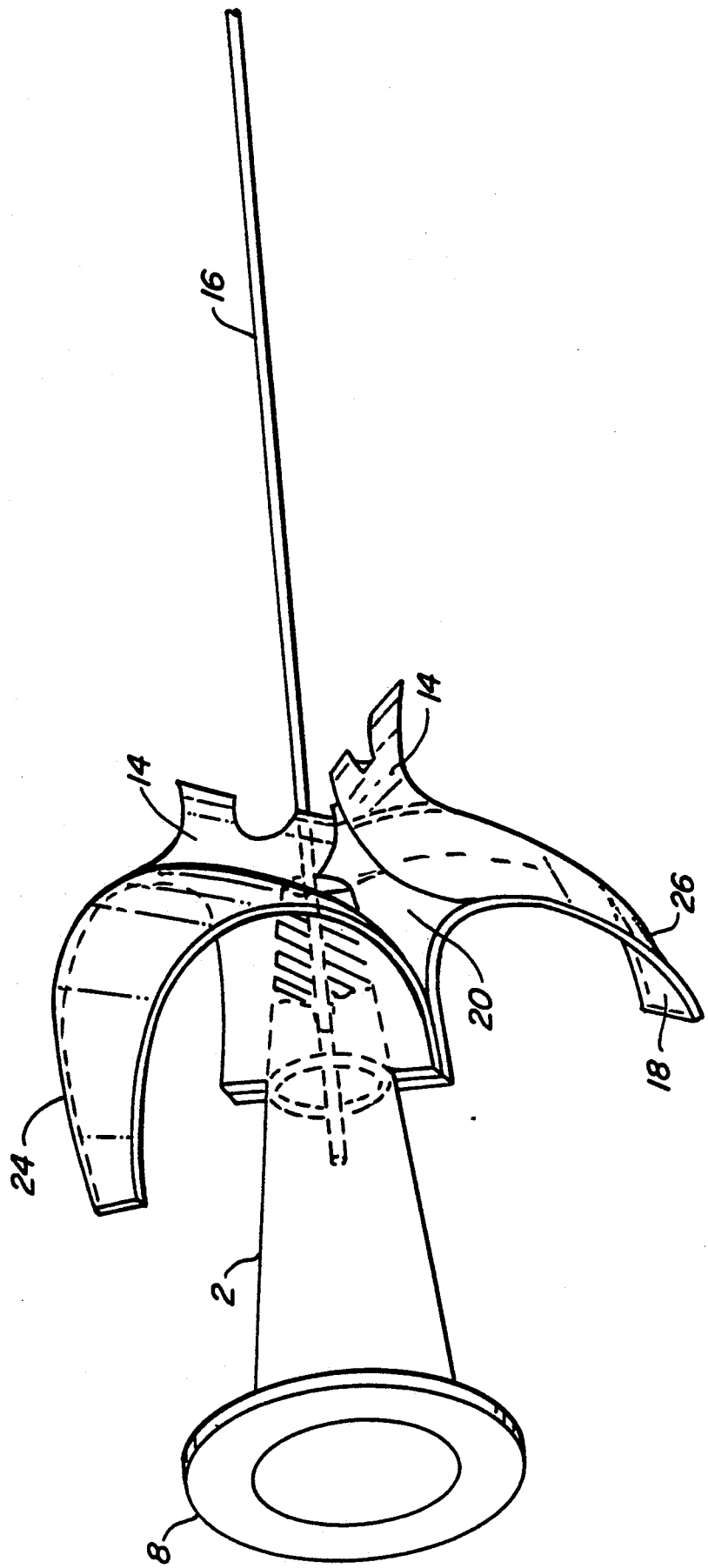
FIG. 2 shows the connector of the present invention as the peel-off covering is being removed to expose the adhesive surface.

The invention provides a connector 1 having a hollow conical body 2 connected to an elongated tail 12. Conical body 2 has an extended rim which forms fingergrip 8. Hollow body 2 gradually narrows or tapers from a wider open end 4 to a narrower open end 6 as it approaches tail 12. Within narrower open end 6 of body 2 is a watertight diaphragm 10 adapted to admit a medical tube 16 and seal the region between diaphragm 10 and tubing 16.

Wider open end 4 is adapted to receive another tube or appliance, such as a drainage bag (not shown). Due to its conical configuration, a number of devices may be received by hollow body 2 at wider end 4. Body 2 could be specially configured to connect to a particular device as well.

Tail 12 comprises two cooperating and co-adapting portions 24/26. Each tail portion 24/26 has an inner surface 20 and an outer surface 18. Tail 12 has an internal groove or passage 28 formed along its length to receive tubing 16. Inner surfaces 20 of cooperating tail portions 24/26 are provided with a strong watertight adhesive which is protected with a peel-away covering 14.

Connector 1 is preferably made of synthetic materials. Conical body 2 is formed of a plastic, such as polyethylene or polypropylene, and diaphragm 10 is elastomeric. Flexible tail 12 is formed of a polyolefin. Removable cover 14 is a plasticized paper. Inner surfaces 20 of cooperating tail portions 24/26 have an adhesive coating of resin. Connector 1 is disposable, and it is presented in a sterile packaged form.

Connector 1 is used as follows. Medical tube 16 exiting from a patient is advanced between co-adapting tail portions 24/26. Tubing 16 is pushed through diaphragm 10 toward wider end 4 of body 2. Protective peel-away coverings 14 are removed from inner surfaces 20 of tail portions 24/26. Exposed inner surfaces 20 are compressed together while capturing tube 16 in passage 28. The adhesive substance holds tail portions 24/26 together securing tube 16 in place. Both diaphragm 10 and tail 12 act to seal the connection between body 2 and tube 16.

First open end 4 receives another tube or channel appropriate to the circumstances and to tubing 16. For example, connector 1 can be connected to a drainage container, such as a Foley bag for urinary flow where tubing 16 is a Foley catheter. Alternatively, connector 1 can couple a variety of tubes to a corresponding apparatus. For instance, if tubing 16 is a chest tube, open end 4 is attached to the entry port for the drainage bottles. If tubing 16 is a nasogastric tube, open end 4 couples with a tube to a suction pump or collection chamber.

Although a preferred embodiment has been described in detail, other applications and modifications within the scope of the invention will be apparent to the ordinary artisan. For example, the connector may connect tubes delivering fluid or medication to the patient, such as intravascular lines. Instead of using plastic to form the hollow body, stainless steel or some other medically compatible material could be used. The device may be adapted for sterilization and reuse instead of being disposable.

Diaphragm 10 may be replaced by other types of seals, preferably ones which also help to secure tube 16 to body 2. For example, this seal could have a one-way valve or a series of projections like brushes or barbs to engage the tubing. The adhesive surface may be modified for a single permanent contact with the tubing, or it may accept repeated engagement. The tail could split into unequal portions or it could be a single strip adapted to wrap around the tubing rather than being laid out like two confronting sheets. Thus, the scope of the invention is not limited by the preceding description, but rather by the following claims.

What is claimed is:

1. A connector for medical tubing comprising:
    a hollow body having first and second ends, the medical tubing and the second end of the body defining a region therebetween when the medical tubing is inserted through the second end;
    a first element mounted to the body and adapted to substantially seal said region when the medical tubing is inserted through the second end; and
    a second element mounted to the body and extending past the second end, the second element including an adhesive surface positioned to adhesively engage the medical tubing extending from the second end to help secure the medical tubing to the hollow body;
    wherein the second element comprises an elongated, flexible and substantially planar sheet in a region extending from the second end of the body away from the first end of the body.

2. The connector of claim 1 wherein a diameter of the hollow body in a vicinity of the first end is larger than a diameter of the hollow body in a vicinity of the second end.

3. The connector of claim 2 wherein the hollow body has a conical configuration.

4. The connector of claim 1 wherein the first element comprises a diaphragm.

5. The connector of claim 4 wherein the diaphragm is formed of an elastomeric material.

6. The connector of claim 1, the second element further comprising an internal groove adapted to receive the medical tubing.

7. The connector of claim 1 wherein the hollow body has an interior and the first element is housed within said interior.

8. The connector of claim 1 wherein the adhesive surface comprises a substance selected from the group including starch, gum, bone, glue, cellulose acetate, casein, sodium silicate, latex, resin, epoxy, and mastic.

9. The connector of claim 1, the second element further comprising first and second sheets wherein each sheet includes an inner and an outer surface, at least one of the inner surfaces including said adhesive surface.

10. The adaptor of claim 9, the second element further comprising a passageway formed between the inner surfaces of the two sheets when the inner surfaces are in contact with each other.

11. A method for preparing an end of medical tubing for subsequent connection to an auxiliary device in a manner to minimize leakage and dislodgement comprising the following steps:
    selecting a connector for medical tubing having a hollow body with open first and second ends, the connector including a first element secured to the body and a second element mounted to the body and extending past the second end, the second element including an adhesive surface and further including an elongated sheet member adapted to receive the medical tubing;

introducing the medical tubing into the connector through the second open end, through the first element and into the causing the first element to seal a region defined between the medical tubing and the second end of the body; and applying the adhesive surface of the second element to the medical tubing extending from the second end to help secure the medical tubing to the body.

12. The method of claim 11 wherein the step of selecting a connector is carried out by selecting a connector with an elastomeric diaphragm as the first element.

13. The method of claim 11 further comprising the step of removing a protective layer from the adhesive surface prior to the applying step.

14. The method of claim 13 further comprising the step of removing the removable layer.

15. A connector for medical tubing comprising:

a hollow body having first and second ends, the medical tubing and the second end of the body defining a region therebetween when the medical tubing is inserted through the second end;

a first element mounted to the body and adapted to substantially seal said region when the medical tubing is inserted through the second end; and a second element mounted to the body and extending past the second end, the second element including an adhesive surface positioned to adhesively engage the medical tubing extending from the second end to help secure the medical tubing to the hollow body, the second element further comprising first and second sheets wherein each sheet includes an inner and an outer surface, at least one of the inner surfaces including said adhesive surface.

* * * * *